(12) United States Patent
Thomson

(10) Patent No.: US 9,989,439 B2
(45) Date of Patent: Jun. 5, 2018

(54) METHOD AND DATA PROCESSING DEVICE FOR SEVERITY ASSESSMENT OF BEARING DEFECTS USING VIBRATION ENERGY

(71) Applicant: Allan Thomson, Lanark (GB)

(72) Inventor: Allan Thomson, Lanark (GB)

(73) Assignee: AKTIEBOLAGET SKF, Gothenburg (SE)

( * ) Notice: Subject to any disclaimer, the term of this patent is extended or adjusted under 35 U.S.C. 154(b) by 5 days.

(21) Appl. No.: 15/294,064

(22) Filed: Oct. 14, 2016

(65) Prior Publication Data
US 2017/0108406 A1 Apr. 20, 2017

(30) Foreign Application Priority Data

Oct. 20, 2015 (GB) .................................. 1518545.7

(51) Int. Cl.
| | |
|---|---|
| G01B 5/28 | (2006.01) |
| G01M 7/00 | (2006.01) |
| G01M 13/04 | (2006.01) |
| G01N 29/44 | (2006.01) |
| G01H 1/00 | (2006.01) |

(52) U.S. Cl.
CPC ............ G01M 13/045 (2013.01); G01H 1/00 (2013.01); G01N 29/4463 (2013.01)

(58) Field of Classification Search
CPC .... G01M 13/045; G01H 1/00; G01N 29/4463
USPC .................... 702/33, 35, 39, 56; 73/659, 660
See application file for complete search history.

(56) References Cited

U.S. PATENT DOCUMENTS

| | | | |
|---|---|---|---|
| 6,293,151 B1* | 9/2001 | Kawamata ........... | G01M 13/045 73/593 |
| 9,032,803 B2* | 5/2015 | Griffaton ............ | G01M 13/045 702/56 |
| 2012/0272736 A1 | 11/2012 | Griffaton | |
| 2014/0039809 A1* | 2/2014 | Girondin .................. | G01H 1/00 702/39 |

FOREIGN PATENT DOCUMENTS

WO         2006043511 A1      4/2006

* cited by examiner

*Primary Examiner* — An Do
(74) *Attorney, Agent, or Firm* — Bryan Peckjian; SKF USA Inc. Patent Dept.

(57) ABSTRACT

Method for detecting bearing defect severity based on bearing rotation speed and at least one data sample of sensor data obtained to measure vibrations of a bearing ring is provided. The method includes converting the data sample from time domain to frequency domain to obtain a signal frequency spectrum; determining a defect center frequency of the bearing using the rotation speed; and identifying a predetermined number of frequency peaks of the signal frequency spectrum. A total vibration energy in an overall frequency band including the predetermined number of frequency peaks is first determined; next, for each of the frequency peaks, a peak energy as a spectral energy of signal components giving rise to the frequency peaks is determined; calculating a bearing defect spectral energy using the peak energies; and finally a ratio of the bearing defect spectral energy and a total vibration energy to assess a defect severity is obtained.

10 Claims, 3 Drawing Sheets

METHOD AND DATA PROCESSING DEVICE FOR SEVERITY ASSESSMENT OF BEARING DEFECTS USING VIBRATION ENERGY

CROSS REFERENCE TO RELATED APPLICATIONS

This application claims priority to British patent application no. 1518545.7 filed on Oct. 20, 2015, the contents of which are fully incorporated herein by reference.

FIELD OF THE INVENTION

The invention relates to the field of condition monitoring in rolling bearings based on acoustic or acceleration measurements.

BACKGROUND OF THE INVENTION

It is known to use acceleration and/or vibration sensors attached to bearing rings of rolling bearings to detect defects in the rolling elements or on the raceways. The sensor data are processed either in a data processing unit integrated in the bearing or attached to the bearing or to its housing or alternatively in a remote monitoring unit.

The bearing condition monitoring technology has been originally conceived for large-size bearings for use e.g. in wind turbines or trains. The scope of applicability of the bearing condition monitoring technology now continuously expands toward bearings of smaller size, e.g. for use in trucks or automobiles and will further expand due to the progress of miniaturization.

Many approaches have been considered ranging from the simple, quantitative rule-based to self-learning neural-network, feature extraction and historically calibrated methods such as novelty detection. However many of the advanced or "smart" methods, though impressive from an academic viewpoint, are lacking in cross industry field experience and the complexity results in bars to the industrial implementation.

In most cases, the methods involve one or more of the measurement tools employing an enveloped (demodulated) vibration signal. These methods include quantitative methods such as detection of the overall amplitude, quantitative statistics (RMS, SD, Variance), counts, periodicity, use of the autocorrelation properties, Hilbert space analysis or Cyclic Time Analysis (CTA). Further known methods include qualitative methods such as characteristic statistics (kurtosis, CF etc.), or methods based on contribution (CTA) fraction or harmonic content fraction.

A problem that affects Condition Monitoring (CM) across all types of machines is at what level Alert and Alarm (Amber and Red) thresholds should be configured for reliable bearing defect detection, in particular when utilizing Acceleration Enveloping measurements. Any method that utilizes the higher frequency ranges of vibration for quantitative (absolute amplitude) assessment of bearing damage severity is plagued with many factors that can significantly amplify or attenuate the amplitudes observed. Hence within these higher frequency ranges the use of fixed quantitative Alert and Alarm thresholds across a range of different applications or even similar applications is unworkable, so individual thresholds are necessary which require many man-hours of an analysts time to fine tune these thresholds from sensor to sensor and from machine to machine.

In the case of rail axle bearing monitoring, the defect frequency amplitudes which are indicative of a bearing with a significant defect can be seen to vary from tenths of a gE to over 10 gE depending on bearing type, axle-box design, sensor location and mounting and sensor orientation. In such rail applications, a common measurement technology is the wireless sensor node for which, when fitted as an aftermarket solution, it is often not feasible to obtain the ideal location and orientation. Also it can be expected that such a RAG (Red Amber Green) method is incorporated into the wireless node.

Vibration measurements collected from rail axle bearings often include a significant amount of external noise, much of which appears to be related to wheel-to-rail interaction which can vary significantly across the different rail applications, tracks, wheel-sets and measurement nodes (inconsistent transfer function). Such external noises often cause an increase in False Positives when using "quantitative" severity methods and thresholds. Whilst "relative" methods with similar external noises would produce an increase in False Negatives. From a CM analyst's point of view or an auto-diagnostic system approach it is preferable to have fewer False Positives even though that might result in a few more False Negatives and often there is a far more clearer separation between CI values when a defect is present than when one is not.

However, up to now, none of these methods achieves the reliability of experienced human engineers looking at the spectrum to detect a defect based on a sequence of harmonics to assess the severity thereof based on the end user risk specifications.

BRIEF SUMMARY OF THE INVENTION

The invention seeks to provide a method enabling an automated bearing vibration condition Severity Rating (SR) value based on vibration Acceleration Enveloping (gE) measurements with improved reliability. A further object of the invention is to enable a simple and uncomplicated adaptation of such a method to application-dependent risk specifications.

The objective of the method is to determine if a bearing is likely to have a raceway defect present by use of an Acceleration Enveloping (or any suitable demodulated acceleration) measurement when both shaft speed and bearing defect frequencies are known.

This object is achieved by a method for detecting a bearing defect severity based on a rotation speed of the bearing and on at least one data sample of sensor data obtained by a sensor configured to measure vibrations of a bearing ring. The method includes the steps of converting the data sample from time domain to frequency domain by applying a Fourier Transform to obtain a signal frequency spectrum; determining a defect center frequency of the bearing using the rotation speed; and identifying a predetermined number of frequency peaks of the signal frequency spectrum.

The inventors propose to improve the known methods for detecting a bearing defect severity by the steps of: determining a total vibration energy in an overall frequency band including the predetermined number of frequency peaks; determining, for each of the frequency peaks, a peak energy as a spectral energy of signal components giving rise to the frequency peaks; calculating a bearing defect spectral energy using the peak energies of the frequency peaks; and using a ratio of the bearing defect spectral energy and the total vibration energy to assess a severity of the bearing defect.

The method according to the invention has proven to be reliable across applications/installations without customizing thresholds, and to be insensitive to sensor calibration deviations and to attenuations from positioning.

Further, the invention features low processing requirements, i.e. keeps sensor node power usage as low as possible, and does not require high ADC requirements (>16 bit or >5120 sps).

The method or the data processing device according to the invention returns a few single overall values indicative of severity and defect type and therefore lends itself to implementation in wireless sensor nodes thanks to the limited transmission power requirements. This further entails complexity at receiver end.

The Percent of Band Overall (PoBO) method according to the invention is an approach that compares the vibration Acceleration Enveloping (gE) spectral energy related to a bearing defect frequency (its fundamental and several harmonics) against the overall energy within a broad band frequency range. This ratio is generally presented as a percentage value for ease of interpretation and threshold configuration.

In calculating the spectral energy associated with a bearing defect it is customary to utilize the first 3 to 5 orders (harmonics) of the defect frequency. Since the signal has been enveloped there is rarely any need to go higher than the 5th order, which already can become a challenge if speed is not accurate enough or there are speed changes during the measurement acquisition.

In the context of the invention, the expression "energy" or "vibration energy" is to be interpreted in a broad sense and covers in particular any suitable quadratic form of the magnitudes of the Fourier transformed frequency spectrum, irrespective of any pre-factors or physical units.

Being a "relative" severity assessment method, the method according to the invention has the following advantages:

1) RAG/alarm thresholds do not need to change across the speed range.

2) RAG/alarm thresholds do not need to change from sensor to sensor due to positioning and orientation differences.

3) Same RAG/alarm thresholds worked across different sensor designs and rail application from freight to high speed passenger.

4) Significant decrease in False-Positives when wheel-rail noise is present and improved trend stability.

5) Improved measurement probability distribution separation between "heathy" and "defective" bearings when compared to the standard CM "quantitative" methods.

In a preferred embodiment of the invention, the step of identifying the predetermined number of frequency peaks includes searching a first frequency peak in a frequency band including the defect center frequency and searching second and subsequent frequency peaks in frequency bands including integer multiples of the defect center frequency.

More preferably, the step of identifying the predetermined number of frequency peaks includes the steps of determining a predetermined number of frequency bands of a first width using the defect center frequency, wherein a first frequency band includes the defect center frequency and the second and following frequency bands include integer multiples of the defect center frequency as their respective window center frequency; determining, for each of the frequency bands, a local maximum of the signal frequency spectrum within the respective frequency band; and determining peak energies of the signal frequency spectrum within each of the frequency bands by calculating a squared sum of an amplitude of the signal frequency spectrum at the local maximum and of the amplitudes of the signal frequency spectrum adjacent to the local maximum. In this context, the adjacent frequencies are the neighboring frequencies in the discrete set of furrier frequencies used for digital processing.

In the preferred embodiment of the invention, the summing includes the next neighbor frequencies. However, in implementations with frequency resolution smaller than the peak width, the number of frequencies should used for summing the energy pertaining to the peak should be chosen such that the entire peak width is covered.

The above method is also referred to as the "basic bandwidth search" method and involves searching for the highest spectral peak within the search bandwidth/frequency bands (i.e. 3%) for each order of the defect frequency. A spectral peak within a search bandwidth is defined as the highest value bin (or frequency) where the bins either side of it have lower values than it.

It does not check that that these spectral peaks are exactly aligned between one order and the next and therefore has been found to be reliable enough where the exact shaft speed and hence also the bearing defects frequencies are known as in such cases the search bandwidth can be kept narrow (<=2%).

However where the shaft speed accuracy is not exact, a wider search bandwidth needs to be used (i.e. >3%) to capture the defect frequencies but this also increases the probability of selecting spectral peaks from other sources that are also within the search bandwidth thus resulting in an erroneously higher PoBO value than reality.

As an alternative approach for identifying the frequency peaks, the inventors propose a further method, which is referred to as "sweep search" in the following.

While the "basic bandwidth search" is easier to implement with limited processing capabilities, the "sweep search" is considered to be more reliable and accurate in a noisy environment (in particular where other harmonic components are present).

Regardless of the how the defect frequency components are determined, the general process remains identical.

The "sweep search" method involves sweeping though each bin in the highest order defect frequency search bandwidth and calculating that 1-bin amplitude or 3-bin RSS for each bin step as though it was a peak and do the same for the corresponding lower orders' matching bins. For each sweep step determine the RSS or SUM of all the orders' values. Then select the sweep step that displays the highest amplitude as being the most representative of a defect.

This "sweep search method" identifies which series of bins being exact harmonic orders have the greatest amount of energy. Hence a single rogue (non-defect related) component present within one of the defect orders' search bandwidth has a reduced probability of being selected if a real defect component with harmonics is present.

In a preferred embodiment of the invention, the step of calculating a bearing defect spectral energy includes calculating a sum, weighted sum or root sum square of the peak energies.

The inventors further propose that the step of determining a total vibration energy in the overall frequency band includes calculating the root squared sum of the magnitudes of the signal frequency spectrum within the frequency band.

According to a further aspect the step of upper limit and the lower limit of the overall frequency band are application dependent settings read from a memory device.

It is further proposed that the method includes the steps of comparing the ratio with at least two threshold values to classify the defect severity into at least three severity classes, and outputting the result. The severity classes could be assigned directly to RAG levels or indirectly, e.g. after applying a hysteresis or "a out of b" approach.

In a preferred embodiment of the invention, the at least two threshold values are application-dependent settings read from a storage device. Being able to select/configure the "band" for reference overall calculation improves trend stability and reduces False-Negatives.

Preferably the defect specific PoBO value is calculated as the ratio as "defect amplitude"/"band overall amplitude"× 100.

If it is desirable to determine the bearing's general condition, the method can be generalized to cover multiple different defect types (inner race, outer race, rolling elements, cage) which can have slightly different weighting on the outcome. These to describe just a few are:

1) The user or system can just select the worst (most severe) of the defect RAG statuses (Green, Amber or Red).

2) A general PoBO value can also be determined by carrying out a RSS of the PoBO values of the multiple different defect types, but suitable "general RAG thresholds" may need to be determined.

3) Calculate an "all defects amplitude" by carrying out a RSS of all the defects "defect amplitudes" then perform the percentage of "band overall" calculation. Suitable "general RAG thresholds" would need to be determined.

Different weightings can be used in the step of calculating a bearing defect spectral energy such as SUM instead of RSS. The person skilled in the art will select the method which provides the most reliable results across environments with differing noise content.

For fixed speed applications where any running speed noise (1×N etc.) is negligible, the "overall frequency band" can be the same for the BPFO, BPFI, BSF and FTF Cls. But if the running speed noise (1×N etc.) is of any significance then the lower limit of the overall frequency bands for BPFO, BPFI and BSF should be selected as to avoid 1×N and 2×N at least. This is highly pertinent for rail axle bearing applications where wheel-to-track noise is often present.

Though a full (avoiding Zero frequency) RSS of the spectrum for the overall value does work reasonably well, the inventors have found that a narrower overall band avoiding the low frequency wheel noises does provide results with slightly better reliability (less sensitive to presence of wheel noises).

However in rail axle bearing applications the speed range selected for the vibration measurements can vary from 50% to 100% of the nominal maximum speed. Below 50% the amount of energy created by a defect can be small and there is often an increase fraction of measurements with noise present. In most rail applications from freight, metro to high speed passenger most of the suitable measurements captured will be between 50% and 100% of the nominal maximum speed for that train on that route.

In alternative embodiments of the invention, the overall frequency band are dependent on the bearing speed such as 2.5× RPM. This has been found to reduce the amount of false negatives due to wheel-rail noises.

A general PoBO RAG configuration, though found to be more reliable than most standard CM detection/severity methods, can be significantly improved by adapting the configuration of several of the method's parameters to suit that specific application. An understanding of how the application operates, speed accuracies and amount and characteristics of background noises is required. Typical configuration changes that can improve reliability of detection and RAG assessment for Rail axle bearings are:

1) Improving Speed Accuracy
   a) Reduced latency
   b) Start, End and Average speeds
   c) Wheel diameters if calculated from GPS ground speed
2) Speed Gating
   a) Within predetermined speed range (normal cruising)
   b) Delta speed lower than predetermined value
3) Position Triggering
   a) Wayside or GPS position triggering on good track section The invention is applicable to any kind of rolling contact bearing including roller bearings, ball bearings, toroidal roller bearings or needle bearings.

The method is suited to any enveloped, demodulated, heterdyned vibration signal with adequate signal-to-noise ratio, in particular but not exclusively to Acceleration Enveloping band-3 spectrum signals.

For each bearing defect the energy associated with a predetermined number of orders of that defect frequency is calculated and then converted into a relative percent value with respect to an "overall" energy from a predetermined frequency band.

In a preferred embodiment, the step of determining the peak level includes calculating a logarithm of the ratio. The logarithm results in a decibel (dB) scale which reflects the human perception and is known to be suitable to differentiate between background fluctuation and the adaptation of threshold levels to user requirements becomes more transparent and convenient.

According to the a further aspect of the invention, the method includes the step of comparing, for each of the peak levels, the ratio with a first predetermined lower threshold value and setting the peak level to zero if the ratio is less than the first predetermined lower threshold value. The lower threshold value should be set such that peak artefacts resulting from random fluctuations are excluded and do not or are unlikely to influence the severity rating.

The inventors further propose that the method includes the step of calculating a sum or weighted sum of the peak levels and to output a quantity proportional to the result of a severity rating for the bearing defect. It has been found that the reliability of the method can be improved by concentrating on not only one of the peaks but further on its higher harmonics to assess the severity.

According to a preferred embodiment of the invention, the method includes the steps of calculating a sum, weighted sum or root squared sum of the peak levels, comparing the result with at least two threshold values to classify the defect severity into at least three severity classes, and outputting the result.

In a preferred embodiment of the invention, the at least two threshold values are application-dependent settings read from a storage device. The two threshold values enable a classification into red-amber-green (RAG) classes of severity, wherein the meaning of the classes is as follows:
   Red=above risk threshold over short term
   Amber=above risk threshold for medium/long term
   Green=no action.

According to a further aspect of the invention, the step of determining peak amplitudes of the signal frequency spectrum in the vicinity of a predetermined number of integer multiples of the defect center frequency includes at least three steps as follows.

In a first step, a predetermined number N of frequency bands of a first width using the defect center frequency is set, wherein a first frequency band includes the defect center frequency and the second and following frequency bands include integer multiples the defect center frequency as their respective window center frequency. In a preferred embodiment of the invention, the multiples are multiples in subsequent natural numbers up to a maximum, which is preferably between 3 and 5. In a second step, a local maximum of the signal frequency spectrum within the respective frequency band is determined for each of the frequency bands. In a third step, peak amplitudes of the signal frequency spectrum within each of the frequency bands are determined using an amplitude of the signal frequency spectrum at the local maximum. The data processing for peak detection can therefore be concentrated to a limited set of frequency bands.

The Acceleration Enveloping (gE) band 3 (500 Hz to 10 kHz) measurements with typical CM configuration for that application should be set with FMax covering at least up to 5×BPFI at the top of the expected speed range, in particular for railway applications.

In order to ensure a reliable result, it is preferred that the speed measurement has an accuracy of 5% or less, most preferably 2% or less. The speed could be calculated based on GPS speed divided by the wheel diameter.

The reliability of the measurements can be improved further by gating of measurements to a specific, application dependent speed band or by gating of measurements to be within a speed stability (start-end delta speed), position dependent gating e.g. by using GPS.

In a preferred embodiment of the invention, the sensor data are Acceleration Enveloping (gE) band-3 data in a band from 500 Hz-10 kHz.

The quality of the condition monitoring results can be further improved by acquisition triggering (i.e. data used only when being taken on a good section of track for rail) and/or by statistical filtering of a set number of buffered measurements. Further, the frequency band can be limited to the surrounding of bearing defect frequencies, wherein the relevant frequency bands can be defined the more precisely the more accurate the bearing defect frequencies can be predicted.

A further aspect of the invention relates to a data processing device configured to execute the method as described above.

In a preferred embodiment of the invention, the data processing devices is integrated in a wireless sensor node which attached to a bearing, in particular to a rail axle bearing.

A yet further aspect of the invention relates to a rolling bearing including a sensor configured to measure vibrations of a bearing ring and a data processing device as mentioned above, wherein the data processing device is configured to process data samples of sensor data obtained by the sensor according to the method as described above.

Last but not least, the invention proposes a condition monitoring system for a machine or a complex device including at least one rolling bearing, a sensor for measuring vibrations of at least one of the rings of the rolling bearing and a data processing device implementing the above in order to determine a vibration condition severity rating using the vibration data obtained from the sensor. While the sensor must be located in sufficiently close mechanical contact to the bearing ring to measure vibrations therein, the data processing device may be located remotely, e.g. in an operator's room of the machine.

The Vibration Severity Model according to the preferred embodiment of invention provides an automated bearing vibration condition Severity Rating (SR) value based on vibration Acceleration Enveloping (gE) measurements, preferably only on gE measurements, and then dependent on the end user risk specifications translates such a severity rating into a Red, Amber and Green (RAG) class. At a later stage, a statistical, a hysteresis, or status logic can be applied to the RAG to improve reliability in particular where measurements are acquired from a changing or noisy environment.

Through their experience, the inventors have established useful severity criteria for the early stages of bearing functional failure that was less amplitude based and more qualitative based using acceleration enveloping (gE) measurements.

Due to the time scales and bearing types (i.e. passenger rail) to create and validate a Red Amber Green (RAG) severity algorithm, the invention provides an automated implementation which is capable of processing the data with short delay.

The above embodiments of the invention as well as the appended claims and figures show multiple characterizing features of the invention in specific combinations. The skilled person will easily be able to consider further combinations or sub-combinations of these features in order to adapt the invention as defined in the claims to his or her specific needs.

DETAILED DESCRIPTION OF THE INVENTION

Figure 1:
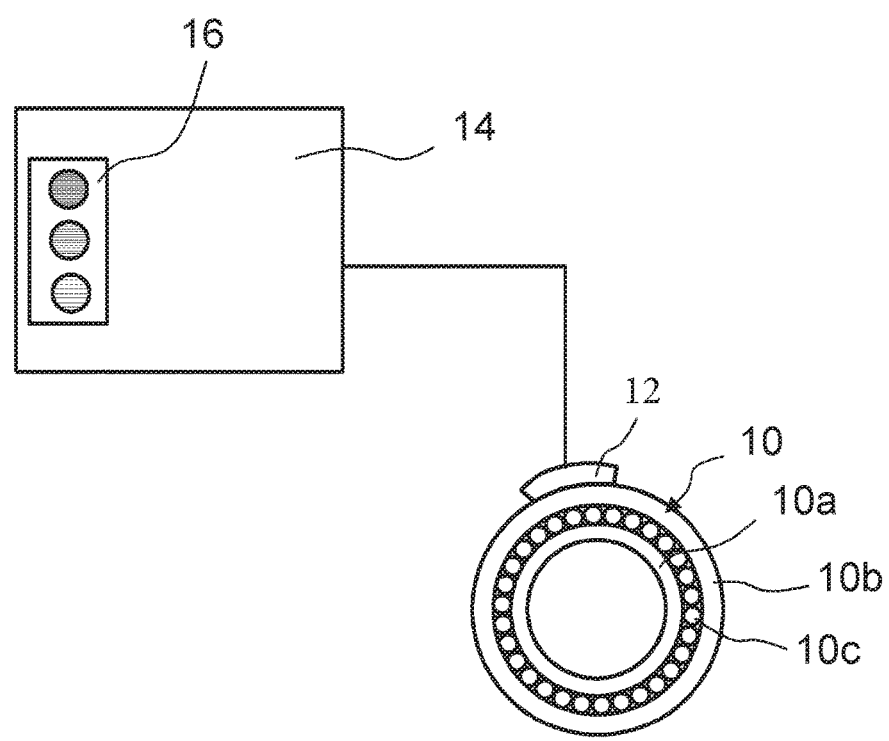
FIG. 1 is a schematic view of a machine equipped with a condition monitoring system according to the invention.

FIG. 1 is a schematic view of a machine including a bearing 10 having an inner ring 10a and an outer ring 10b and at least one row of rolling elements 10c arranged between the inner ring 10a and the outer ring 10b, wherein the rolling elements 10c roll on the inner raceway of the inner ring 10a and on the outer raceway of the outer ring 10b. The bearing 10 is equipped with an acceleration sensor 12 configured to measure vibrations of the outer ring 10b of the bearing 10.

The machine is equipped with a condition monitoring system according to the invention, which includes the sensor 12, a data processing device 14 and a signal output device 16 such as a warning lamp or a monitor. The sensor data obtained by the sensor 12 include background noise and a regular, quasi-periodic, frequency- and load-dependent contribution of the passing rolling elements 10c.

In the embodiment of FIG. 1, the data processing device 14 is connected to the sensor 12 by a wire. However, the sensor data could be transmitted in a wireless way or the data processing device 14 could be integrated into a single unit together with the sensor 12, wherein the result of the data processing (the defect severity rating) could be output by lamps or a LCD display provided in the unit and/or using a wired or wireless data connection.

In the event that a defect exists on the inner raceway on the inner ring 10a, on the outer raceway on the outer ring 10b, or on the rolling surface of one of the rolling elements 10c, this defect will create an acoustic shock wave propagating through the outer ring 10b to the sensor 12 and resulting in a peak in the sensor signal.

These peaks are repeated in a periodical pattern with a characteristic frequency which is proportional to the relative rotation speed of the bearing rings and which depends on the nature of the defect. The repetition rate of shock waves emanating from defects on the outer raceway is the Ball Pass Frequency at the Outer Ring (BPFO), the repetition rate of shock waves emanating from defects on the inner raceway is the Ball Pass frequency at the Inner Ring (BPFI) and the repetition rate of shock waves emanating from defects on the rolling elements surface is the Ball Spin Frequency (BSF). The proportionality factor between these repetition rates and the bearing running speed (RPM) is also referred to as order of running speed DO, and depends on the various diameters and can be derived using geometrical considerations.

The following description is limited to the detection and assessment of severity of defects on the outer raceway but the invention can be easily extended to other defect types or multiple defect types in combination, if desired.

Figure 2:
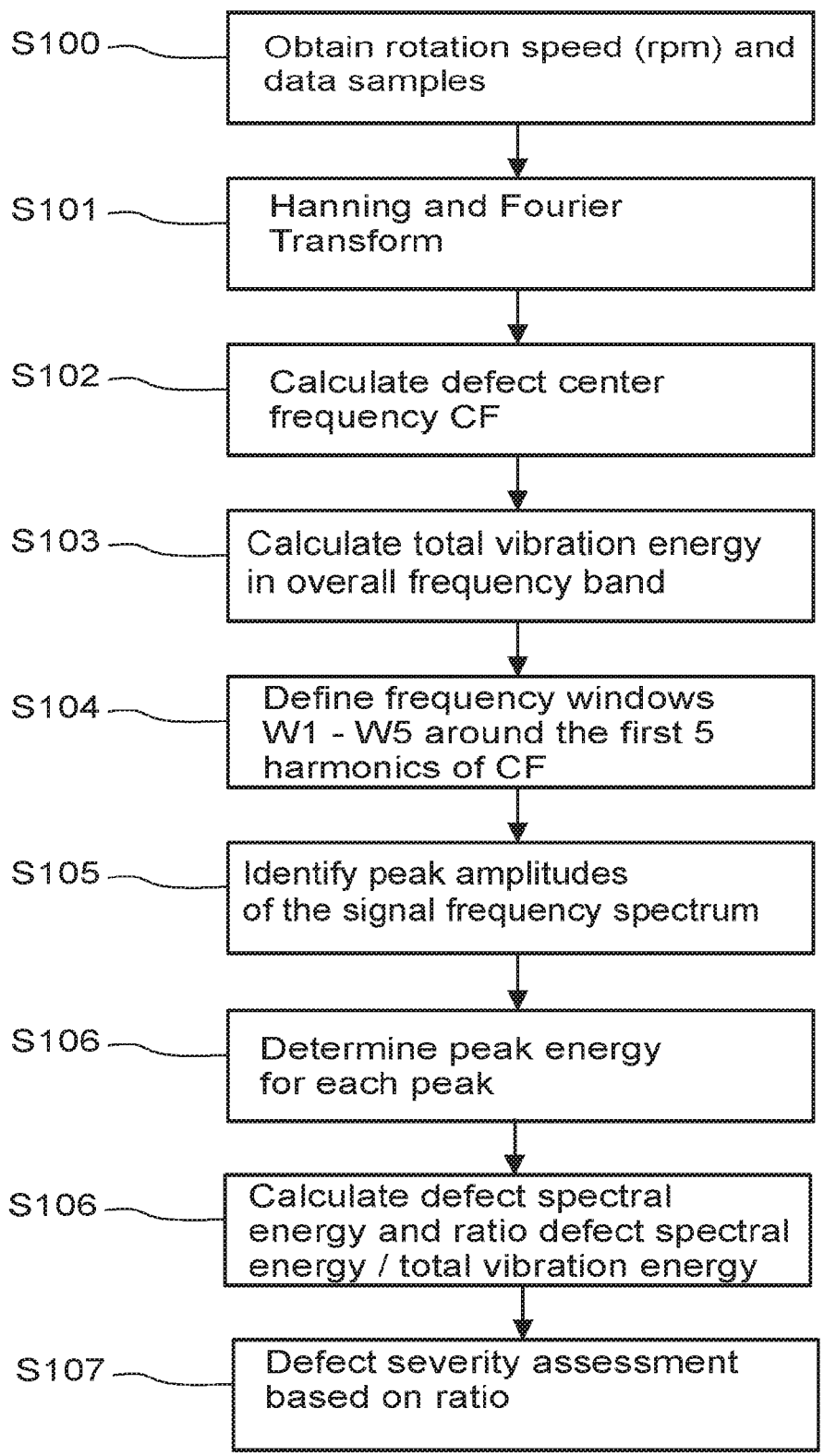
FIG. 2 is a flowchart of a method for detecting a bearing defect severity according to the invention.

The data processing device 14 of the condition monitoring system of FIG. 1 reads the data samples of sensor data obtained by the sensor 12 and processes these data samples using the method for detecting a bearing defect severity according to the invention, which is illustrated in more detail in FIG. 2.

In a step S100, the data processing device 14 obtains a rotation speed (RPM) of the bearing and a plurality of data samples of length 2N of sensor data obtained by the vibration sensor 12 in a step S100. The rotation speed can be derived from the sensor data by the data processing device 14 (e.g. by measuring the BPFO and calculating the rotation speed therefrom) or the rotation speed may be provided independently.

The method then proceeds in a step S101 with optional pre-processing (Filtering, Hanning window or the like) and then converting the data sample from time domain to frequency domain by applying a Fourier Transform—preferably a Fast Fourier Transform FFT—to obtain a signal frequency spectrum.

In one embodiment of the invention, the sensor data are input as a gE waveform of 2N samples (S) and acquisition duration of (t) seconds. The input is converted from the time domain to frequency domain by first applying the Hanning Window then the Fast Fourier Transform (FFT) returning an array of Magnitude values (FFTM). The results may optionally be subjected scaling or correction factors if required.

The resulting data frequency spectrum has a number of FFT values V=S+1, a Nyquist frequency (last value) of F=S/(t×2) and a delta frequency per FFT line of Fd=1/t (Note; first value is at 0 Hz).

In the next step S102, the method detects a defect center frequency CF of the bearing 10 using the rotation speed RPM by multiplying the rotation speed obtained as explained above by a predetermined proportionality factor DO.

Being provided with the bearing defect such as BPFO and BPFI as an order of running speed (DO) and speed in RPM (N), the bearing defect frequency is determined by:

Defect center frequency in Hz CF=DO×N/60

The method then proceeds to step S103 and calculates a total vibration energy in an overall frequency band including at least the defect center frequency CF and its fivefold value 5×CF.

The method then defines in a step S104 a sequence of frequency bands W1-W5 to be analyzed in order to identify peak amplitudes of the signal frequency spectrum in the vicinity of a predetermined number of integer multiples of the defect center frequency.

To this end, a predetermined number N of frequency bands of a first width using the defect center frequency CF is set. A first frequency band W1 includes the defect center frequency CF and the second and following frequency bands W2 . . . W5 include integer multiples 2×CF . . . 5×CF of the defect center frequency CF as their respective window center frequency. The widths of the frequency bands W1-W5 are expressed as a percentage of the respective window center frequencies CF-5×CF, but may have other functional dependencies or may or of the sample length, the sampling rate and/and time span of the signal in alternative embodiments.

In the preferred embodiment of the invention, the multiples are multiples in subsequent natural numbers up to a maximum and 5, i.e. the window center frequency are equal to BPFO, 2*BPFO, 3*BPFO, 4*BPFO, and 5*BPFO. Generally, satisfactory results in determining a bearing' raceway defect severity can be obtained by considering only the first 5 orders of the defect's fundamental component/frequency.

In other words, provided with a percentage +/−bandwidth (BW) within to extract the 1× and 2× defect amplitudes, the boundaries of the frequency bands W1-W5 as FFT magnitude array indexes are given by:—

1× low boundary BL1=ROUND(CF×(1−BW/100)/Fd)

1× high boundary BH1=ROUND(CF×(1+BW/100)/Fd)

2× low boundary BL2=ROUND(2×CF×(1−BW/100)/Fd)

2× high boundary BH2=ROUND(2×CF×(1+BW/100)/Fd)

And so on to the fifth order.

Figure 3:
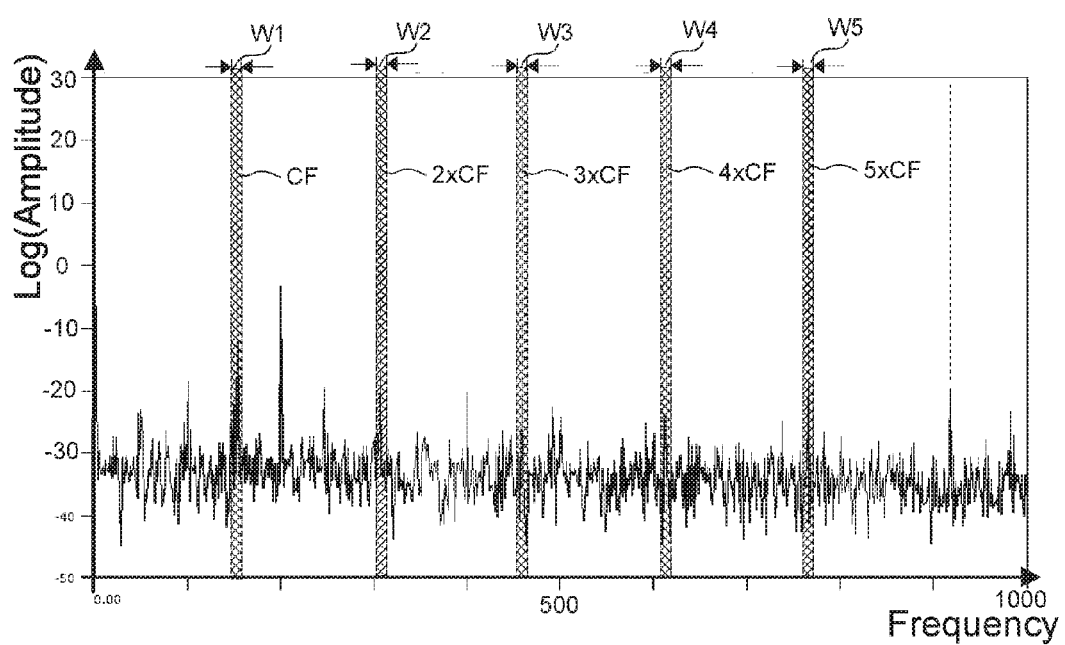
FIG. 3 is a signal spectrum with the harmonics of a defect center frequency and the pertinent frequency bands.

A typical signal spectrum with the harmonics of the defect center frequency CF and the pertinent frequency bands W1-W5 is illustrated in FIG. 3.

If the severity assessment is to be done for multiple defect types in parallel (e.g. BPFO, BPFI, BSF, steps S102 and S103 can be repeated for the pertinent values of DO.

In a step S105 in FIG. 2, local maxima of the signal frequency spectrum within the respective frequency band W1-W5 are determined for each of the frequency bands W1-W5 and identified as frequency peaks. A local maximum is detected if a magnitude in the array data representing the frequency spectrum is has two neighboring values which are smaller than the value itself. If the fluctuation width is high, the data may be pre-processed using a suitable filter prior to localizing a maximum. Maximum values located at the edge of a frequency band should be discarded.

In a preferred embodiment, the detection of the local maximum is achieved as follows:

Within each of the frequency bands as defined above, the Root Sum Squared RSS of the two highest adjacent values of the highest peak within the boundary is calculated.

To avoid selecting the edge values of a boundary of the frequency band as a peak (such as when the boundary is in a valley) if the highest value within the frequency band is either of the edge values it is converted to zero.

This is repeated again so if the now highest value within the frequency band is either of the edge values it is also converted to zero.

The remaining highest value is considered to be the peak maximum.

Otherwise, the "sweep search" method described above could be used to identify the maximum within the frequency band.

Once the maxima are identified, the peak energy is calculated for each of the frequency peaks in the signal frequency spectrum within each of the frequency bands are determined using an amplitude of the signal frequency spectrum at the local maximum. The peak energy is calculated by taking the squared sum of set of magnitudes for a narrow frequency, band centered on the local maximum, e.g. the squared sum of the maximum magnitude and the magnitudes at its two neighboring frequency bins.

Other known peak identification algorithms might be used in alternative embodiments of the invention.

The data processing for peak detection and peak energy calculation can thus be concentrated to a limited set of frequency bands. The peak energy calculation is performed for each of the frequency peaks identified in step 104.

In the following step S106, a bearing defect spectral energy using the peak energies of the frequency peaks by summing over the individual peak energies and a ratio of the bearing defect spectral energy and the total vibration energy is calculated.

In the severity assessment step S107, the ratio is output as the severity level to a memory device, to data logger or to a remote condition monitoring server.

The ratio is then compared with at least two threshold values to classify the defect severity into at least three severity classes, and the result is output. The two threshold values are application-dependent settings read from a storage device.

The two threshold values enable a classification into red-amber-green (RAG) classes of severity, wherein the Green class corresponds to values below both threshold values or equal to the lower threshold value, the Amber class corresponds to values between the two threshold values and the Red class corresponds to values above both of the threshold values including the higher one of the threshold values.

These threshold values can be altered to suit the stated acceptable risk levels associated with that specific application and to have a reliable detection/diagnosis, i.e. with suitably low numbers of False-Negatives and False-Positives.

The inventors further propose to improve the reliability of the condition monitoring alarm method according to the invention by applying a suitable alarm or RAG status logic to the most recent datasets (last several measurements). These can be done by a statistical method (i.e. distribution), the common "IN and OUT hysteresis" or the "Most-out-of" 5, 7 or 11 method. Due to the type and occurrence distribution of wheel-to-rail noise in the measurements when monitoring rail axle bearings the "Most-out-of" method has proven to work more satisfactory than the "IN and OUT hysteresis" method.

The severity rating value is determined by an algorithm from the measurement characteristics and ranges from 1 (as new) to 10 (bearing collapse). The RAG class is determined by another algorithm from the SR value, the application (considering measurement location, defect sensitivity, speed, load etc.) and the acceptable operational risk limits provided by the end user or application standard. Operational risk is defined as the probability of a "functional failure" within a given operational period multiplied by the consequences of such "functional failure" often expressed as a financial value or as a result of a 3×3 to 5×5 matrix of probability x consequences.

The invention provides a reliable data processing method for condition monitoring of rolling bearings applicable to gE band-3 data from sensor units known to obtain passenger rail axle bearing data, freight train endcap sensor data or retrofit sensor unit for aftermarket purposes. The invention is applicable to any condition monitoring system employing an Acceleration Enveloping band-3 standard and can be transferred to other sensor nodes for use in bearings. The invention enables the detection of bearing raceway failures at early stage through detection of defects on an outer raceway or n an inner raceway of the bearing and the detection of advanced bearing failures by cage defect or integrity issues. Further, the invention enables a reliable detection of rolling element defects.

As an output, the invention provides a reliable gE measurement severity rating, e.g. from 1 to 10 and a Red, Amber, Green classification of the severity rating where:

Both the severity rating and the Red, Amber, Green classification can be adapted to the application-dependent risk specifications in an easy way by simply setting the threshold values employed.

The invention claimed is:

1. A method for detecting a bearing defect severity based on a rotation speed of a bearing and on at least one data sample of sensor data obtained by a sensor configured to measure vibrations of a bearing ring, the method comprises the steps of:
   a. converting the data sample from time domain to frequency domain by applying a Fourier Transform to obtain a signal frequency spectrum;
   b. determining a defect center frequency of the bearing using the rotation speed;
   c. identifying a predetermined number of frequency peaks of the signal frequency spectrum;
   d. determining a total vibration energy in an overall frequency band including the predetermined number of frequency peaks;
   e. determining, for each of the frequency peaks, a peak energy as a spectral energy of signal components giving rise to the frequency peaks;
   f. calculating a bearing defect spectral energy using the peak energies of the frequency peaks; and
   g. using a ratio of the bearing defect spectral energy and the total vibration energy to assess a severity of the bearing defect.

2. The method according to claim 1, wherein the step of identifying the predetermined number of frequency peaks includes searching a first frequency peak in a frequency band including the defect center frequency and searching second and subsequent frequency peaks in frequency bands including integer multiples of the defect center frequency.

3. The method according to claim 1, wherein the step of identifying the predetermined number of frequency peaks includes the steps of:
   a. determining a predetermined number of frequency bands (W1-W5) of a first width using the defect center frequency, wherein a first frequency band includes the defect center frequency and the second and following frequency bands include integer multiples the defect center frequency as their respective window center frequency;
   b. determining, for each of the frequency bands (W1-W5), a local maximum of the signal frequency spectrum within the respective frequency band (W1-W5); and c. determining peak energies of the signal frequency spectrum within each of the frequency bands (W1-W5) by calculating a squared sum of an amplitude of the signal frequency spectrum at the local maximum and of the amplitudes of the signal frequency spectrum adjacent to the local maximum.

4. The method according to claim 1, wherein the step of calculating a bearing defect spectral energy includes of calculating a sum, weighted sum or root sum square of the peak energies.

5. The method according to claim 1, wherein the step of determining a total vibration energy in the overall frequency band includes calculating the root squared sum of the magnitudes of the signal frequency spectrum within the frequency band.

6. The method according to claim 1, wherein the step of upper limit and the lower limit of the overall frequency band are application dependent settings read from a memory device.

7. The method according to claim 1, further comprising the steps of:
   a. comparing the ratio with at least two threshold values to classify the defect severity into at least three severity classes, and
   b. outputting the result.

8. The method according to claim 7, wherein the at least two threshold values are application-dependent settings read from a storage device.

9. A condition monitoring system for monitoring a machine comprising:
   at least one bearing equipped with a sensor configured to measure vibrations of a bearing ring, and
   a data processing device, wherein the data processing device is configured to process data samples of sensor data obtained by the sensor by converting the data sample from time domain to frequency domain by applying a Fourier Transform to obtain a signal frequency spectrum; determining a defect center frequency of the bearing using the rotation speed; identifying a predetermined number of frequency peaks of the signal frequency spectrum; determining a total vibration energy in an overall frequency band including the predetermined number of frequency peaks; determining, for each of the frequency peaks, a peak energy as a spectral energy of signal components giving rise to the frequency peaks; calculating a bearing defect spectral energy using the peak energies of the frequency peaks; and using a ratio of the bearing defect spectral energy and the total vibration energy to assess a severity of the bearing defect.

10. A machine comprising:
    at least one bearing equipped with a sensor, and
    a condition monitoring system having at least one bearing equipped with a sensor configured to measure vibrations of a bearing ring, and
    a data processing device, wherein the data processing device is configured to process data samples of sensor data obtained by the sensor by converting the data sample from time domain to frequency domain by applying a Fourier Transform to obtain a signal frequency spectrum; determining a defect center frequency of the bearing using the rotation speed; identifying a predetermined number of frequency peaks of the signal frequency spectrum; determining a total vibration energy in an overall frequency band including the predetermined number of frequency peaks; determining, for each of the frequency peaks, a peak energy as a spectral energy of signal components giving rise to the frequency peaks; calculating a bearing defect spectral energy using the peak energies of the frequency peaks; and using a ratio of the bearing defect spectral energy and the total vibration energy to assess a severity of the bearing defect, wherein
    the data processing device of the condition monitoring system is configured to process data samples of sensor data obtained by the sensor.

* * * * *